US008288167B2

(12) United States Patent
Sundararajan et al.

(10) Patent No.: US 8,288,167 B2
(45) Date of Patent: Oct. 16, 2012

(54) CHEMILUMINESCENCE SENSOR ARRAY

(75) Inventors: Narayan Sundararajan, San Francisco, CA (US); Tae-Woong Koo, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 459 days.

(21) Appl. No.: 12/471,286

(22) Filed: May 22, 2009

(65) Prior Publication Data
US 2010/0055713 A1  Mar. 4, 2010

Related U.S. Application Data

(62) Division of application No. 11/321,050, filed on Dec. 30, 2005, now Pat. No. 7,537,934.

(51) Int. Cl.
*G01N 21/76* (2006.01)

(52) U.S. Cl. ...... 436/172; 436/164; 435/7.1; 435/283.1; 435/287.1; 435/287.2; 435/288.7; 422/68.1; 422/82.05; 422/82.08

(58) Field of Classification Search .................. 435/7.1, 435/283.1, 287.1, 287.2, 288.7, 288.3; 422/50, 422/52, 61, 68.1, 82.05, 82.08; 436/164, 436/172
See application file for complete search history.

(56) References Cited

U.S. PATENT DOCUMENTS

| 5,244,630 | A | 9/1993 | Khalil et al. |
| 5,653,539 | A | 8/1997 | Rosengaus |
| 6,087,114 | A | 7/2000 | Rider |
| 6,331,441 | B1 | 12/2001 | Balch et al. |
| 6,379,969 | B1 | 4/2002 | Mauze et al. |
| 6,432,662 | B1 | 8/2002 | Davis et al. |
| 2003/0003587 | A1 | 1/2003 | Murray |
| 2005/0113658 | A1 | 5/2005 | Jacobson et al. |

*Primary Examiner* — Melanie J Yu
(74) *Attorney, Agent, or Firm* — Pillsbury Winthrop Shaw Pittman LLP

(57) ABSTRACT

Embodiments of the invention relate to integrated chemiluminescence devices and methods for monitoring molecular binding utilizing these devices and methods. These devices and methods can be used, for example, to identify antigen binding to antibodies. The devices include both a chemiluminescence material and a detector integrated together.

11 Claims, 3 Drawing Sheets

CHEMILUMINESCENCE SENSOR ARRAY

REFERENCE TO RELATED APPLICATION

This application is a divisional of U.S. patent application Ser. No. 11/321,050 filed Dec. 30, 2005 now U.S. Pat. No. 7,537,934, the contents of which is hereby incorporated by reference in its entirety.

FIELD OF INVENTION

The embodiments of the invention relate to integrated chemiluminescence devices and methods for monitoring molecular binding utilizing these devices and methods. These devices and methods can be used, for example, to identify antigen binding to antibodies. The invention transcends several scientific disciplines such as polymer chemistry, biochemistry, molecular biology, medicine and medical diagnostics.

BACKGROUND

FIG. 1 shows a typical "sandwich" assay for identifying and quantifying an antigen. This is called a sandwich assay because it uses 2 or more antibodies to sandwich the antigen. In the typical sandwich assay a primary antibody is bound to a support substrate. This primary antibody is used as a capture antibody to capture a specific antigen in solution. A second antibody that attaches to the same antigen as the primary antibody is then added. This second antibody includes a tag of some sort for identifying the presence of the second antibody attached to the antigen. This tag may include, for example, a complex that fluoresces when exposed to laser light. This fluorescent signal can then be detected by a separate light detector.

One Example of a sandwich assay is an Enzyme-Linked Immunosorbent Assay (ELISA or EIA for short). The ELISA assay utilizes two antibodies, one of which is specific to the antigen and the other of which is coupled to an enzyme. This second antibody gives the assay its "enzyme-linked" name. The enzyme promotes a reaction involving an enzyme converted substrate, which produces a signal that can be proportional to the amount of the antigen that is present.

One drawback of the sandwich assay technique is the number of steps that are typically required to carry out the technique. For example, at least the following steps are typically performed: 1) Prepare a surface plate to which a known quantity of antibody is bound; 2) Apply the antigen-containing sample to the plate; 3) Wash the plate, so that unbound antigen is removed, 4) Apply the enzyme-linked antibodies which are also specific to the antigen; 5) Wash the plate, so that unbound enzyme-linked antibodies are removed; 6) Apply a chemical which is converted by the enzyme into a chemical that can generate fluorescent or color signal; and 7) View the result: if it fluoresces, then the sample contained antigen.

In addition to the number of steps, several separate specialized compositions and devices are used in the sandwich assay technique. For example, two different antibodies are used and a separate detector for detecting the fluorescence is used.

DETAILED DESCRIPTION

Figure 1:
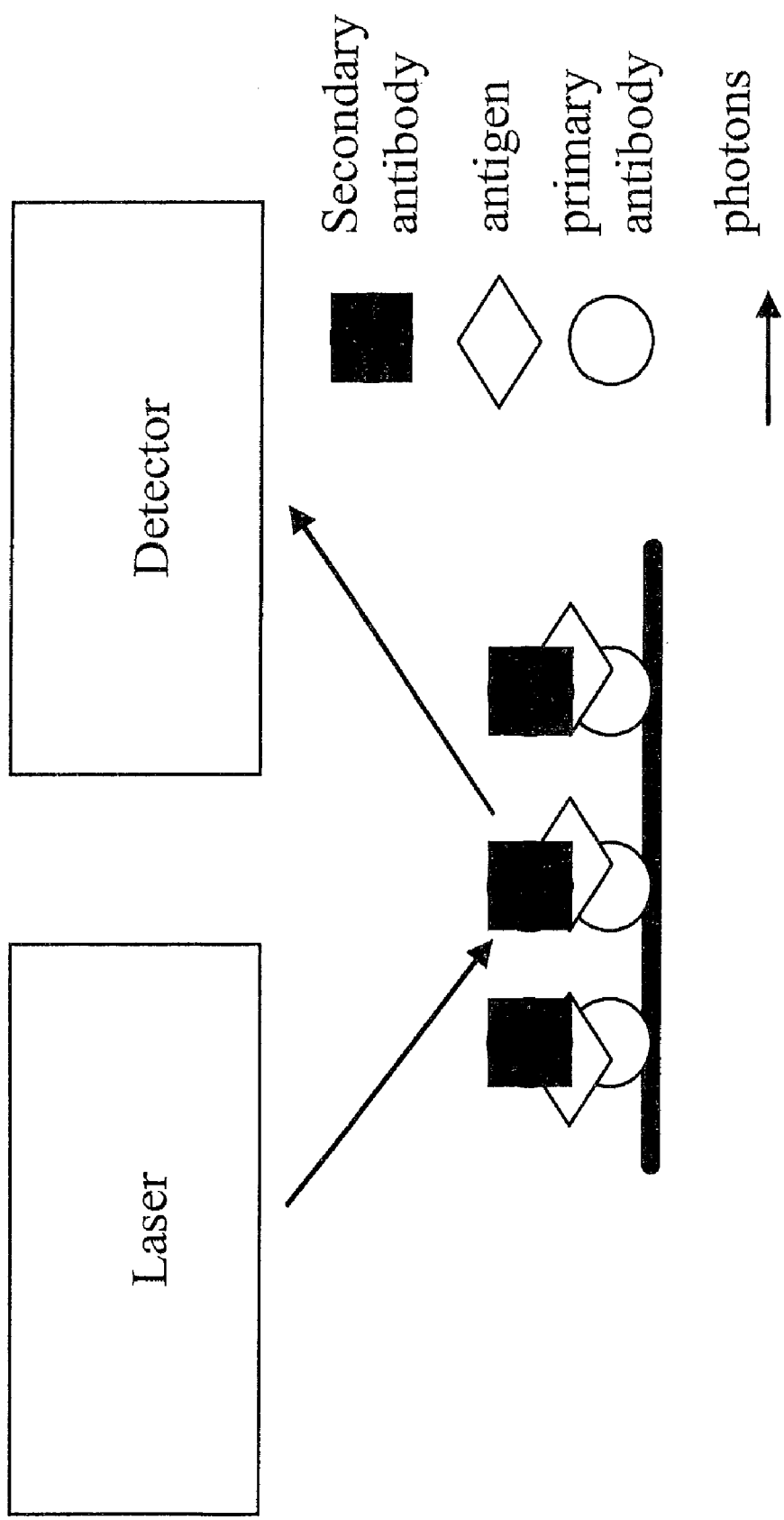
FIG. 1 shows a sandwich assay for identifying and quantifying an antigen.

As used in the specification and claims, the singular forms "a", "an" and "the" include plural references unless the context clearly dictates otherwise. For example, the term "an array" may include a plurality of arrays unless the context clearly dictates otherwise.

An "array," "macroarray" or "microarray" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns. A multiple-well array is a support that includes multiple chambers for containing sample spots.

"Solid support," "support," and "support substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations. The support may be made from a variety of materials including glass, nickel, magnetic metal, gold, silicon, nitrocellulose, or Polyvinylidene Difluoride (PVDF).

The term "analyte", "target" or "target molecule" refers to a molecule of interest that is to be analyzed and can be any molecule or compound. Some examples of analytes may include a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The analyte molecule may be fluorescently labeled DNA or RNA.

An analyte can be in the solid, liquid, gaseous or vapor phase. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase can be changed by pressure, temperature as well as by affecting surface tension of a liquid by the presence of or addition of salts etc.

The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus. In certain aspects of the invention, the analyte is charged.

A member of a specific binding pair ("sbp member") is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Specific binding is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-enzyme converted substrate interactions, polynucleotide hybridization interactions, and so forth.

Non-specific binding is non-covalent binding between molecules that is relatively independent of specific surface structures, Non-specific binding may result from several factors including hydrophobic interactions between molecules.

The methods of the present invention may be used to detect the presence of a particular target analyte, for example, a nucleic acid, oligonucleotide, protein, enzyme, antibody or antigen. The methods may also be used to screen bioactive agents, i.e. drug candidates, for binding to a particular target or to detect agents like pollutants.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The term analyte further includes polynucleotide analytes such as those polynucleotides defined below. These include m-RNA, r-RNA, t-RNA, DNA, DNA-RNA duplexes, etc.

The term analyte also includes receptors that are polynucleotide binding agents, such as, for example, peptide nucleic acids (PNA), restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the solid substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules, (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

The term "capture molecule" refers to a molecule that is immobilized on a surface. The capture molecule is generally, but not necessarily, binds to a target or target molecule. The capture molecule is typically a nucleotide, an oligonucleotide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be fluorescently labeled DNA or RNA. The capture molecule may or may not be capable of binding to just the target molecule or just the probe molecule.

The term "molecule" generally refers to a macromolecule or polymer as described herein. However, arrays comprising single molecules, as opposed to macromolecules or polymers, are also within the scope of the embodiments of the invention.

"Predefined region" or "spot" or "pad" refers to a localized area on a solid support. The spot could be intended to be used for formation of a selected molecule and is otherwise referred to herein in the alternative as a "selected" region. The spot may have any convenient shape, e.g., circular, rectangular, elliptical, wedge-shaped, etc. For the sake of brevity herein, "predefined regions" are sometimes referred to simply as "regions" or "spots." In some embodiments, a predefined region and, therefore, the area upon which each distinct molecule is synthesized is smaller than about 1 cm$^2$ or less than 1 mm$^2$, and still more preferably less than 0.5 mm$^2$. In most preferred embodiments the regions have an area less than about 10,000 µm$^2$ or, more preferably, less than 100 µm$^2$, and even more preferably less than 10 µm$^2$ or less than 1 µm$^2$. Additionally, multiple copies of the polymer will typically be synthesized within any preselected region. The number of copies can be in the hundreds to the millions. A spot could contain an electrode to generate an electrochemical reagent, a working electrode to synthesize a polymer and a confinement electrode to confine the generated electrochemical reagent. The electrode to generate the electrochemical reagent could be of any shape, including, for example, circular, flat disk shaped and hemisphere shaped.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers."

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the N$^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme converted substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The term "fluid" used herein means an aggregate of matter that has the tendency to assume the shape of its container, for example a liquid or gas. Analytes in fluid form can include fluid suspensions and solutions of solid particle analytes.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers.

The term "biopolymer" is a polymer found in nature and includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids.

The term "Antigen" referers to the proteins that can be recognized (bound) by an antibody. Antigens are most commonly polypeptides or carbohydrates, but they can also be lipids, nucleic acids, or even small molecules like neurotransmitters. A particular antibody molecule can typically only interact with a small region of an antigen and in the case of a polypeptide this is generally about 5-12 amino acids. This region can be continuous or it can be distributed in different regions of a primary structure that are brought together because of the secondary or tertiary structure of the antigen. The region of an antigen that is recognized by an antibody is called an epitope. In some cases, it is possible to make an antibody that is directed against the antigen binding site of another antibody (i.e., the antigen binding site is the epitope). This type of antibody is called an anti-idiotype antibody. In this case, the antigen binding site of the anti-idiotype antibody can be similar in structure to the original antigen (they both recognise the same antibody.)

Embodiments of the invention relate to integrated chemiluminescence devices and methods for monitoring molecular binding utilizing these devices and methods. These devices and methods can be used, for example, to identify antigen binding to antibodies. The devices include both a chemiluminescence material and a detector integrated together.

More specifically, one embodiment is an integrated assay device. The device includes a chemiluminescent material, a biopolymer, and a light detector. An activity of the biopolymer can activate the chemiluminescent material and the activity of the chemiluminescent material can be detected by the light detector. Preferably, the biopolymer is an antibody.

Preferably, the device further includes a support substrate, wherein the chemiluminescent material, the biopolymer; and the light detector are on the support substrate. Preferably, the support substrate comprises glass, nickel, magnetic metal, gold, silicon, nitrocellulose, or polyvinylidene difluoride (PVDF).

Preferably, the antibody includes a conjugate enzyme for activating the chemiluminescent material. A preferred conjugate enzyme is horseradish peroxidase. Preferably, the antibody is capable of activating the chemiluminescent material upon binding to an antigen. Preferably, the antibody is configured to bind to an antigen of interest.

Preferred chemiluminescent materials include diacylhydrazides. Alternatively, the chemiluminescent material may include luminol, N-(4-Aminobutyl)-N-ethylisoluminol, 4-Aminophthalhydrazide monohydrate, Bis(2-carbopentyloxy-3,5,6-trichlorophenyl) oxalate, 9,10-Bis(phenylethynyl)anthracene, 5,12-Bis(phenylethynyl)naphthacene, 2-Chloro-9,10-bis(phenylethynyl)anthracene, 1,8-Dichloro-9,10-bis(phenylethynyl)anthracene, Lucifer Yellow CH dipotassium salt, Lucifer yellow VS dilithium salt, 85% (dye content), 2,4,5-Triphenylimidazole, 9,10-Diphenylanthracene, Rubrene, or Tetrakis(dimethylamino)ethylene.

Preferably, the light detector is a charge-coupled device (CCD) or a complimentary metal-oxide semiconductor (CMOS).

Another embodiment is a method of making an integrated device. The method includes applying a chemiluminescent material to a support substrate including a light detector, and applying a biopolymer to the support. Another embodiment of a method of making an integrated device includes attaching a light detector to a support comprising a chemiluminescent material and a biopolymer. Preferably, the biopolymer is an antibody.

Yet another embodiment is a method of detecting an antigen. The method includes introducing an analyte antigen to a device comprising a chemiluminescent material, an antibody that binds to a target antigen and a light detector. The chemiluminescent material luminesces if the analyte antigen is the target antigen.

Figure 2:
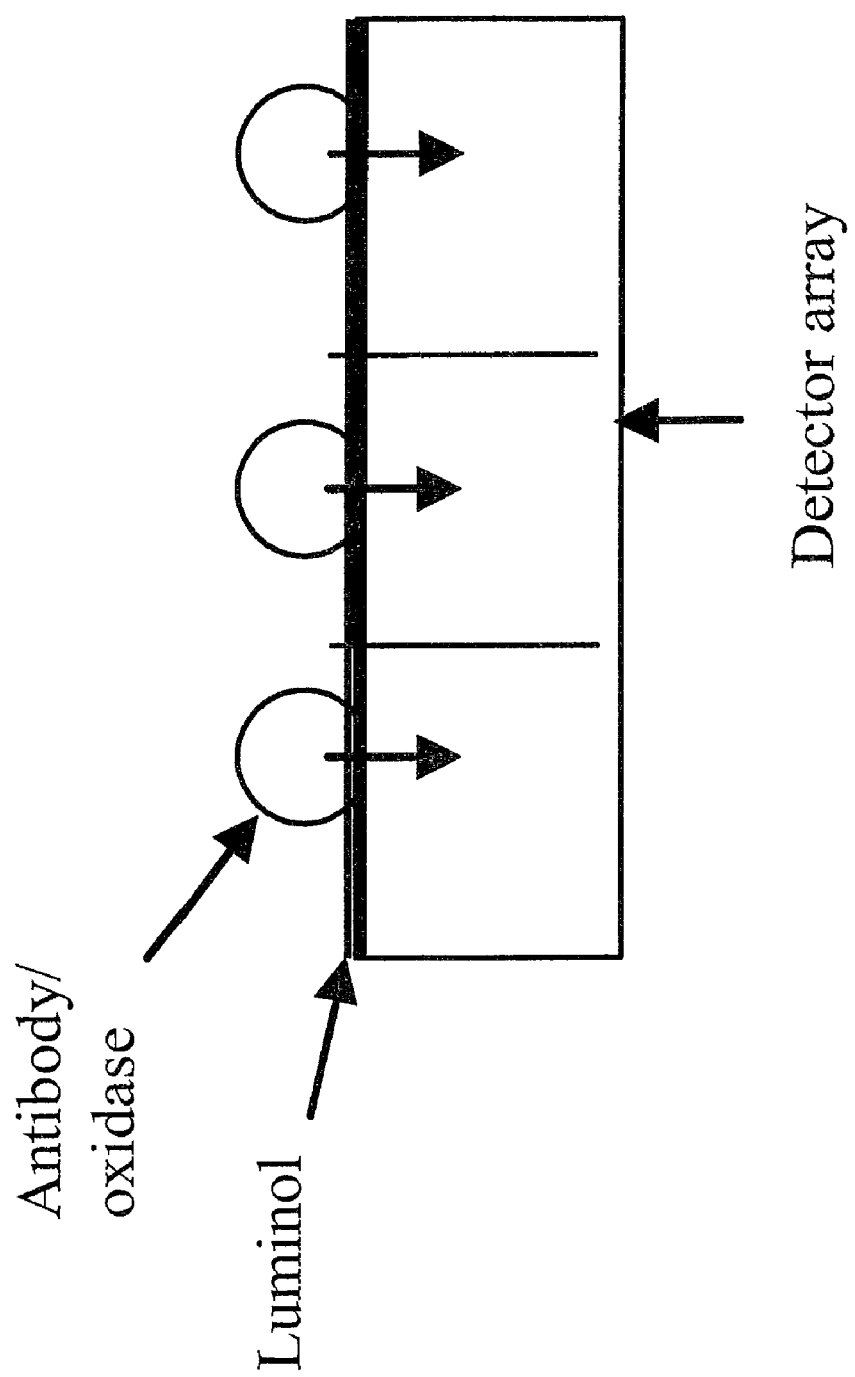
FIG. 2 shows an embodiment of an integrated chemiluminescence device and detector according to this invention.

Further aspects of the embodiments will be described in more details with reference to FIGS. 2 and 3. One embodiment of a preferred device is shown in FIG. 2 and includes a detector array and a chemiluminescent material. A chemiluminescent material provides for chemiluminescence when activated. Preferred materials are cyclic diacylhydrazides such as luminol, which are activated by oxidation, Luminol is typically activated by the horseradish peroxidase (HRP)/hydrogen peroxide catalysed oxidation in alkaline conditions. Immediately following oxidation, the luminol is in an excited state which then decays to ground state via a light emitting pathway. Enhanced chemiluminescence is preferably achieved by performing the oxidation of luminol by the HRP in the presence of chemical enhancers such as phenols. This has the effect of increasing the light output approximately 1000 fold and extending the time of light emission. The light produced by this enhanced chemiluminescent reaction peaks after 5-20 minutes and decays slowly thereafter with a half life of approximately 60 minutes.

Preferably the chemiluminescent material is applied to the same support substrate as the detector. The support substrate can comprise multiple layers and may include silicon, glass, silicon dioxide, transparent polymers, 3D polymer gels, gold, and silver, etc. In this manner, an integrated miniaturized assay device can be prepared in advance of assay testing. An integrated device as used herein is a single device in which the component parts of the device are designed to be used together as a single device and none of the components of the device are designed to be used alone. Since the detector and the chemiluminescent material are part of the same device, researchers can more easily and accurately perform assay analysis with little additional equipment.

Any light detector that is able to detect the chemiluminescence of the material can be used. Preferred detectors are CCD (charge-coupled device) and CMOS (complimentary metal-oxide semiconductor) sensors. Both CCD and CMOS detectors convert light produced by the chemiluminescent material into electrons using an array of pixels. In a CCD detector, the charge produced from the detector is actually transported across the chip and read at one corner of an array. An analog-to-digital converter can then be used to turn each pixel's value into a digital value. In most CMOS devices, there are several transistors at each pixel that amplify and move the charge using more traditional wires. The CMOS approach may be more flexible because each pixel can be read individually. Accordingly, a CMOS array can be used to detect several different antigens simultaneously as different parts of the array can be configured to detect different antigens.

Standard methods for producing CMOS arrays and CCD detectors can be utilized to produce the light detectors. The chemiluminescent material can then be dispersed in an inert polymer matrix and applied by spin coating or spray coating directly on top of the light detector substrate with functional groups for attachment of the antibody molecules. These could be, for example, carboxylic acid groups for amine attachment of antibodies. The thickness of the chemiluminescent material doped polymer matrix can be adjusted by spin coating speed. Antibody can be conjugated to the polymer matrix via functional groups, for example, carboxylic or aldehyde groups.

Alternatively, the top of the CMOS detector substrate with functional groups can be coated with the chemiluminescent material and the antibody can then be applied by spotting. The spotting is typically done by dipping a spotting needle into the antibody solution and bringing the spotting needle near contact with the substrate at locations where the antibodies are desired. The size of the antibody spot is determined by the size of the spotting needle and the volume of antibody solution retained by the spotting needle.

As shown in FIG. 2, an antibody that includes conjugate tag for activating the chemiluminescent material is preferably applied onto the chemiluminescent material. For example an antibody that includes an oxidase enzyme conjugate can be used to activate a device that includes luminol. A preferred oxidase enzyme is HRP. Other preferred oxidase enzymes include Myeloperoxidase, Glutathione Peroxidase, Cholesterol Oxidase f. *Pseudomonas*, Cholesterol Oxidase from *Nocardia erythropolis*, Choline Oxidase from *Alcaligenes* sp, D-Amino acid Oxidase from hog kidney, D-Amino acid Oxidase from hog kidney, Glycerol 3-phosphate Oxidase from *Aerococcus viridans*, L-Amino acid Oxidase from *Crotalus adamanteus*, Lipoxidase from soybean, lyophilized, powder, Sarcosine Oxidase from *Pseudomonas* sp., and Xanthine Oxidase from buttermilk, lyophilized. Different antibodies may be applied to different parts of the support substrate to allow for the simultaneous detection of different antigens.

In an alternative embodiment, the chemiluminescent material and the antibody that includes a tag for activating the chemiluminescent material can be applied to a support substrate. The support substrate can then be analyzed using a separate non integrated detector.

Figure 3:
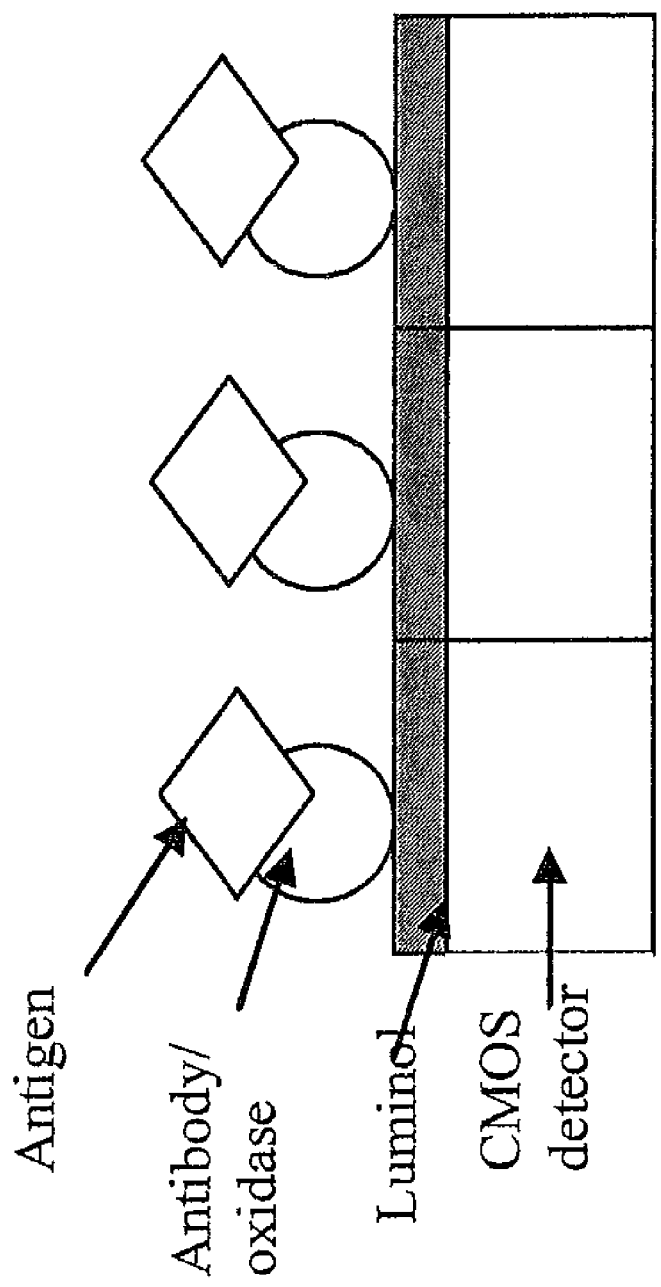
FIG. 3 shows an embodiment of an integrated chemiluminescence device and detector including an antigen according to this invention.

The operation of the device is shown in FIG. 3. In FIG. 3 an antigen attaches to the antibody in an exothermic reaction. The exothermic reaction provides the energy for the oxidase enzyme attached to the antibody to oxidize the chemiluminescent material. The luminescene produced by the chemiluminescent material can then be detected by the detector.

Specifically, if the oxidase oxidizes the chemiluminescence material, light is emitted from the chemiluminescence material layer. The emitted light is converted to electrons in the light detector, and the electrons are read out as electrical signal by the light detector. The electrical signal can be further amplified or processed by a microprocessor or in an electrical circuit, or stored in a solid state device such as a flash memory or a storage media like an optical disk or a hard drive.

In an alternative embodiment, the device utilizes a light source for stronger signal generation. The light source is positioned at an angle so that the direct illumination from the light source is not detected by the CMOS or CCD detector. Preferred light sources include light emitting diodes (LED), incandescent light bulbs, fluorescence light bulbs, gas lamps including mercury, argon, neon, and krypton lamps, and halogen and xenon lamps.

In another alternative embodiment, the light source can be positioned directly above the substrate. In this case, an optical filter may be positioned between the chemiluminescence layer and the CMOS or CCD, to block the light from the light source while transmitting light generated by the oxidizing chemiluminescence material. Preferred optical filters include thin film filters, for example, Bragg filters or any other interference filters, and absorption/reflection filters that absorb or reflect specific wavelength of light.

The device may also include micro-fluid channels for delivering a sample to the device. Alternatively, samples may be applied to the device through spotting techniques.

The devices and methods described herein can be used for a variety of applicants, for example, in the point of care and field devices for diagnostics, forensic, pharmaceutical, agricultural, food inspection, biodefense, environmental monitoring, and industrial process monitoring.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A method of making an integrated device comprising:
applying a chemiluminescent material to a support substrate comprising a light detector;
applying a biopolymer to the support substrate;
wherein the biopolymer is configured to activate the chemiluminescent material and the light detector is configured to detect an activity of the chemiluminescent material, and wherein the chemiluminescent material is applied directly on the light detector.

2. The method of claim 1, wherein the biopolymer is an antibody.

3. The method of claim 1, wherein the support substrate comprises glass, nickel, magnetic metal, gold, silicon, nitrocellulose, or polyvinylidene difluoride (PVDF).

4. The method of claim 2, wherein the antibody comprises a conjugate enzyme for activating the chemiluminescent material.

5. The method of claim 4, wherein the conjugate enzyme is horseradish peroxidase.

6. The method of claim 2, wherein the antibody is capable of activating the chemiluminescent material upon binding to an antigen.

7. The method of claim 2, wherein the antibody is configured to bind to an antigen of interest.

8. The method of claim 1, wherein the chemiluminescent material comprises a cyclic diacylhydrazides.

9. The method of claim 1, wherein the chemiluminescent material comprises a material selected from the group consisting of luminol, N-(4-Aminobutyl)-N-ethylisoluminol, 4-Aminophthalhydrazide monohydrate, Bis(2-carbopentyloxy-3,5,6-trichlorophenoyxl)oxalate, 9,10-Bis(phenylethynyl)anthracene, 5,12-Bis(phenylethynyl)naphthacene, 2-Chloro-9,10-bis(phenylethynyl)anthracene, 1,s-Dichloro-9,10-bis(phenylethynyl)anthracene, Lucifer Yellow CH dipotassium salt, Lucifer yellow VS dilithium salt, 85% (dye content), 2,4,5-Triphenylimidazole, 9,10-Diphenylanthracene, Rubrene, and Tetrakis(dimethylamino)ethylene.

10. The method of claim 1, wherein the light detector is a charge-coupled device (CCD) or a complimentary metal-oxide semiconductor (CMOS).

11. A method of making an integrated device comprising:
applying a chemiluminescent material to a support substrate comprising a light detector;
applying a biopolymer to the support substrate;
wherein the biopolymer is configured to activate the chemiluminescent material and the light detector is configured to detect an activity of the chemiluminescent material, and wherein the chemiluminescent material is applied directly on the light detector;
wherein an activity of the biopolymer can activate the chemiluminescent material and activity of the chemiluminescent material can be detected by the light detector, wherein a layer of chemiluminescent material is applied directly on the light detector of the support substrate.

* * * * *